United States Patent
Vigouroux Elie et al.

(10) Patent No.: US 11,471,397 B2
(45) Date of Patent: Oct. 18, 2022

(54) PROCESS FOR THE PREPARATION OF MICROCAPSULES

(71) Applicant: Firmenich SA, Geneva (CH)

(72) Inventors: Florence Vigouroux Elie, Geneva (CH); Sonia Godefroy, Geneva (CH); Murray Osborne, Geneva (CH)

(73) Assignee: Firmenich SA, Satigny (CH)

( * ) Notice: Subject to any disclaimer, the term of this patent is extended or adjusted under 35 U.S.C. 154(b) by 418 days.

(21) Appl. No.: 16/319,876

(22) PCT Filed: Jul. 26, 2017

(86) PCT No.: PCT/EP2017/068904
§ 371 (c)(1),
(2) Date: Jan. 23, 2019

(87) PCT Pub. No.: WO2018/019894
PCT Pub. Date: Feb. 1, 2018

(65) Prior Publication Data
US 2019/0269603 A1    Sep. 5, 2019

(30) Foreign Application Priority Data

Jul. 27, 2016   (EP) .................................... 16181447

(51) Int. Cl.
*A61K 8/87* (2006.01)
*A61K 8/11* (2006.01)
(Continued)

(52) U.S. Cl.
CPC ................ *A61K 8/87* (2013.01); *A01N 25/28* (2013.01); *A23L 27/72* (2016.08); *A61K 8/11* (2013.01);
(Continued)

(58) Field of Classification Search
CPC ....................................................... A61K 8/87
See application file for complete search history.

(56) References Cited

U.S. PATENT DOCUMENTS

| 3,577,515 A | 5/1971 | Vandegaer |
| 4,145,184 A * | 3/1979 | Brain ..................... C11D 3/505 |
| | | 8/137 |

(Continued)

FOREIGN PATENT DOCUMENTS

| CN | 103331133 A | 10/2013 |
| CN | 104938500 A | 9/2015 |

(Continued)

OTHER PUBLICATIONS

Product webpage for VORANATE M 580 [online], accessed on (Apr. 24, 2021) and retrieved from the URL <https://www.dow.com/content/dcc/en-us/document-viewer.html?docType=salesSpec&contentType=salesSpec&title=VORANATE%E2%84%A2+M+580+Polymeric+MDI&tradeProduct=000000003738&product=3738z&language=en>.*
International Search Report and Written Opinion, application PCT/EP2017/068904, dated Sep. 8, 2017.
Ken Terao et al., Colloids and Surfaces B Biointerfaces, vol. 37, Issues 3-4, Sep. 1, 2004, pp. 129-132.

*Primary Examiner* — Benjamin J Packard
(74) *Attorney, Agent, or Firm* — Armstrong Teasdale LLP (57) ABSTRACT

The present invention relates to a new process for the preparation of microcapsules. Microcapsules obtainable by said process are also an object of the invention. Perfuming compositions and consumer products comprising said capsules, in particular perfumed consumer products in the form of home care or personal care products, are also part of the invention.

14 Claims, 6 Drawing Sheets

(51) Int. Cl.
  *A61K 8/64* (2006.01)
  *A61K 8/73* (2006.01)
  *A61Q 13/00* (2006.01)
  *A61Q 19/10* (2006.01)
  *C11D 3/37* (2006.01)
  *A01N 25/28* (2006.01)
  *A61K 8/84* (2006.01)
  *A23L 27/00* (2016.01)
  *C11D 17/00* (2006.01)
  *A61K 8/65* (2006.01)
  *A61K 9/50* (2006.01)
  *C11D 3/50* (2006.01)
  *B01J 13/16* (2006.01)
  *B01J 13/20* (2006.01)

(52) U.S. Cl.
  CPC ............... *A61K 8/64* (2013.01); *A61K 8/645* (2013.01); *A61K 8/65* (2013.01); *A61K 8/731* (2013.01); *A61K 8/732* (2013.01); *A61K 8/84* (2013.01); *A61K 9/5031* (2013.01); *A61K 9/5089* (2013.01); *A61Q 13/00* (2013.01); *A61Q 19/10* (2013.01); *C11D 3/3703* (2013.01); *C11D 3/3726* (2013.01); *C11D 3/505* (2013.01); *C11D 17/0039* (2013.01); *A61K 2800/412* (2013.01); *A61K 2800/594* (2013.01); *A61K 2800/805* (2013.01); *B01J 13/16* (2013.01); *B01J 13/206* (2013.01)

(56) References Cited

U.S. PATENT DOCUMENTS

| | | | | |
|---|---|---|---|---|
| 4,847,152 A | * | 7/1989 | Jabs | B41M 5/165 428/402.21 |
| 6,090,886 A | * | 7/2000 | Konno | C08G 18/0823 524/819 |
| 2007/0042182 A1 | * | 2/2007 | Markus | B01J 13/16 428/402.2 |
| 2015/0252312 A1 | | 9/2015 | De Villeneuve et al. | |

FOREIGN PATENT DOCUMENTS

| | | | | |
|---|---|---|---|---|
| DE | 2342066 | A1 | 3/1974 | |
| DE | 2342066 | A1 | 3/1994 | |
| EP | 633059 | A1 | 1/1995 | |
| JP | S42771 | A | 1/1967 | |
| JP | S51119683 | A | 10/1976 | |
| JP | H03173565 | A | 7/1991 | |
| JP | H06175388 | A | 6/1994 | |
| WO | 1994029603 | A1 | 12/1994 | |
| WO | 1997044125 | A1 | 11/1997 | |
| WO | 2004098767 | A1 | 11/2004 | |
| WO | 2011154893 | A1 | 12/2011 | |
| WO | 2013000587 | A1 | 1/2013 | |
| WO | WO-2014194600 | A1 * | 12/2014 | B01J 13/14 |

* cited by examiner

PROCESS FOR THE PREPARATION OF MICROCAPSULES

CROSS-REFERENCE

This application is a 371 filing of International Patent Application PCT/EP2017/068904 filed 26 Jul. 2017, which claims the benefit of European patent application 16181447.0, filed 27 Jul. 2016, the contents of which are hereby incorporated by reference in their entirety.

TECHNICAL FIELD

The present invention relates to a new process for the preparation of microcapsules. Microcapsules obtainable by said process are also an object of the invention. Perfuming compositions and consumer products comprising said microcapsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. This is referred to as performance in terms of stability for the delivery system. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule shell remains intact, the encapsulated active tends to leak out of the capsule by diffusion through the shell due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule shells, with chemical groups such as polyamines and polyisocyanates, has been described as a way to improve stability of microcapsules. WO2011/154893 discloses for instance a process for the preparation of polyurea microcapsules using a combination of aromatic and aliphatic polyisocyanates in specific relative concentrations. Compared to aminoplast, polyurea-based microcapsules present the additional advantage of being free from melamine-formaldehyde. However, these capsules are not always satisfactory in terms of mechanical properties as that are not friable, which can negatively impact their olfactive performance represented by the odor intensity perceived during handling and after intentional breakage e.g. by rubbing.

On the other hand, some prior arts have been describing polyurea-based microcapsules prepared in absence of added polyamine. In particular, WO97/44125 discloses microcapsules prepared by interfacial polymerization process in which polyurea is formed only from an aromatic diisocyanate described as the essential component to form the capsule shell. In this disclosure, an aromatic polyisocyanate having 3 or more isocyanate groups is optionally present but only used as a cross-linking agent. However, although diisocyanates are known to be very reactive and therefore attractive to form a polymeric shell, there are not always considered as suitable component from a safety standpoint. It has been further taught in *Single-particle light scattering study of polyethyleneglycol-grafted poly(ureaurethane) microcapsule in ethanol*, from Ken Terao et al, in Colloids and Surfaces B: Biointerfaces 37 (2004) 129.132 that capsules based on the use of high levels of triisocyanate to make a capsule shell compared to the quantity of oil to be encapsulated showed poor oil retention upon aging. More particularly, according to this article, even if close to an equiweight of polyisocyanate is used to encapsulate large, high log P molecule (di-2-ethylhexylphtalate) expected to show low propension to leakage through a thick capsule shell, the obtained capsules show poor storage stability when placed in organic solvent, with very high leakage of the (di-2-ethylhexylphtalate) out of the capsule, thus suggesting the polyisocyanate (triisocyanate) used is not suited to yield shell capable of preventing core oil leakage in tough media potentially inducing leakage, be organic solvent or aqueous solutions with high levels of surfactants.

Thus, although core-shell microcapsules are known in the art, the quality of these capsules and/or the way to manufacture them could be improved.

There is therefore still a need to provide polyurea-based capsules prepared by simplified and cost-effective processes that would be olfactively performing and stable in challenging media such as surfactant-based consumer products.

SUMMARY OF THE INVENTION

It has now been found, that contrary to what could be expected based on prior teachings, performing polyurea-based microcapsules encapsulating a hydrophobic active ingredient such as a perfume oil could be obtained with a shell essentially formed from a polyisocyanate other than a diisocyanate. The process of the invention therefore provides a solution to the above-mentioned problems as it allows preparing capsules in the absence of an additional cross-linker with a membrane consisting of polymerised polyisocyanate essentially formed from a polyisocyanate comprising at least three isocyanate functional groups, preferably aromatic and free from diisocyanate. Unexpectedly, even with very limited amounts of such polyisocyanate used, those capsules demonstrate a high performance in terms of stability and olfactive performance.

In a first aspect, the present invention relates to a process for the preparation of a polyurea-based core-shell microcapsule slurry comprising the steps of:
1) admixing a hydrophobic active ingredient with at least one polyisocyanate having at least three isocyanate functional groups to form an oil phase, provided that the oil phase is essentially free from diisocyanate;
2) dissolving an ionic or non-ionic emulsifier in water to form a water phase, wherein the ionic emulsifier is chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudocollagen, Biopolymer SA-N, Pentacare-NA PF, and mixtures thereof and wherein the non-ionic emulsifier is chosen in the group consisting of polyvinyl alcohol, modified polyvinyl alcohol, modified starch, modified cellulose, polysaccharides, and mixtures thereof;

3) adding the oil phase to the water phase to form an oil-in-water dispersion;

4) applying conditions sufficient to induce interfacial polymerisation to form microcapsules in form of a slurry; said process being characterized in that:
   the at least one polyisocyanate having at least three isocyanate functional groups is present in an amount comprised between 1 and 15 wt % of the oil phase,
   no substantial amount of amine or polyamine is added at any stage of the process, and
   it does not comprise a further step of adding a cationic polymer to form an outer coating to the microcapsule.

In a second aspect, the invention relates to a polyurea-based microcapsule slurry obtainable by the process described above.

In a third aspect, the present invention relates to a polyurea-based microcapsule powder obtained by drying the microcapsule slurry as defined above.

In a fourth aspect, the present invention relates to a microcapsule slurry comprising polyurea-based microcapsules having a core-shell morphology and comprising
   an oil-based core comprising a hydrophobic active ingredient;
   a shell consisting essentially of polymerised polyisocyanate formed from at least on polyisocyanate comprising at least three isocyanate functional groups and an emulsifier as defined above in the absence of an amine or a polyamine, wherein the microcapsule does not comprise a cationic coating.

In a fifth aspect, the invention concerns a perfuming composition comprising
   (i) microcapsules as defined above, wherein the oil comprises a perfume;
   (ii) at least one ingredient selected from the group consisting of a perfumery carrier and a perfumery co-ingredient; and
   (iii) optionally at least one perfumery adjuvant, Finally, in a sixth and seventh aspects, the invention relates to a surfactant-based consumer perfumed product in liquid or powder form, containing microcapsules or a perfuming composition as previously defined.

DETAILED DESCRIPTION OF THE INVENTION

Unless stated otherwise, percentages (%) are meant to designate a percentage by weight of a composition.

By "perfume or flavour oil", it is meant a single perfuming or flavouring compound or a mixture of several perfuming or flavouring compounds.

For the sake of clarity, by the expression "dispersion" in the present invention it is meant a system in which particles are dispersed in a continuous phase of a different composition and it specifically includes a suspension or an emulsion.

A "core-shell microcapsule", or the similar, in the present invention it is meant that capsules have a particle size distribution in the micron range (e.g. a mean diameter (d(v, 0.5)) comprised between about 1 and 3000 µm) and comprise an external solid oligomers-based shell or shell and an internal continuous oil phase enclosed by the external shell. In other words bodies like coacervates or extrudates (i.e. porous solid phases containing droplets of a liquid) are not part of the invention.

According to the invention, the wordings "mean diameter" or "mean size" are used indifferently.

According to the invention, "no substantial amount of amine or polyamine" means that the amount of amine or polyamine added has to be sufficiently low so as not to be able to significantly change the properties of the microcapsule shell if it reacts with the polyisocyanate. Typically, the amount of amine functionalities that can be added in the process of the present invention is less than 50% molar, preferably less than 25% molar, most preferably less than 10% molar of the amount of isocyanate functionalities.

According to a particular embodiment, no amine or polyamine is added at any stage of the process.

By "polyurea-based" wall or shell, it is meant that the polymeric shell comprises urea linkages produced by either an amino-functional crosslinker or hydrolysis of isocyanate groups to produce amino groups capable of further reacting with isocyanate groups during interfacial polymerization. Thus, urethane linkages produced by reaction of a polyol with the isocyanate groups during interfacial polymerization are excluded from the definition.

In the context of the invention, additional cross-linker or additional cross-linking agent is meant to designate a spacer capable of linking polymeric chains among each other.

According to the invention, the oil phase is essentially free from diisocyanate.

According to a particular embodiment, the oil phase is completely free from diisocyanate.

According to the invention, the microcapsules are free from melamine-formaldehyde.

It has been found that microcapsules with a good performance namely a right balance between stability in a surfactant-based product and odor perception, could be obtained without adding a cross-linker, namely a (poly)amine to a process that is based on interfacial polymerisation of a particular polyisocyanate used in limited amounts. This is very surprising in view of the fact that the only processes describing polyurea-based capsules without the addition of a polyamine so far were either using a diisocyanate as an essential ingredient due to its reactivity, or were teaching away from using triisocyanate as the obtained capsules were then described as having a low performance in particular high oil leakage upon storage.

The present invention therefore relates in a first aspect to a process for the preparation of a polyurea-based core-shell microcapsule slurry comprising the steps of:
1) admixing a hydrophobic active ingredient with at least one polyisocyanate having at least three isocyanate functional groups to form an oil phase, provided that the oil phase is essentially free from diisocyanate;
2) dissolving an ionic or non-ionic emulsifier in water to form a water phase, wherein the ionic emulsifier is chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudocollagen, Biopolymer SA-N, Pentacare-NA PF, and mixtures thereof and wherein the non-ionic emulsifier is chosen in the group consisting of polyvinyl alcohol, modified polyvinyl alcohol, modified starch, modified cellulose, polysaccharides, and mixtures thereof;
3) adding the oil phase to the water phase to form an oil-in-water dispersion;
4) applying conditions sufficient to induce interfacial polymerisation to form microcapsules in form of a slurry; said process being characterized in that:
    the at least one polyisocyanate having at least three isocyanate functional groups is present in an amount comprised between 1 and 15 wt % of the oil phase,
    no substantial amount of amine or polyamine is added at any stage of the process, and it does not comprise a further step of adding a cationic polymer to form an outer coating to the microcapsule.

According to an embodiment, no substantial amount of other water-soluble reactant than amine or polyamine susceptible to polymerize with the polyisocyanate is added at any stage of the process, said water-soluble reactant being chosen in the group consisting of polyols, thiols, ureas, urethanes and mixtures thereof.

It has been thus found that in the absence of a diisocyanate, a polyisocyanate comprising at least three isocyanate functional groups—preferably aromatics—even present in limited amount in the oil phase was capable of polymerisation with sufficient efficiency to provide a capsule shell with good properties.

Step 1: Providing an Oil Phase

In the first step of the process, a hydrophobic active ingredient is admixed with at least one polyisocyanate having at least three isocyanate functional groups to form an oil phase, provided that the oil phase is essentially free from diisocyanate.

Hydrophobic Active Ingredient

By "hydrophophic active ingredient", it is meant any active ingredient—single ingredient or a mixture of ingredients—which forms a two-phases solution in water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the oil phase do not warrant a more detailed description here, which in any case would not be exhaustive, the skilled person being able to select them on the basis of its general knowledge and according to intended use or application.

Examples of such insect control agents are birch, DEET (N,N-diethyl-m-toluamide), essential oil of the lemon *eucalyptus* (*Corymbia citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to an embodiment, the hydrophobic active ingredient represents between 20 to 50% by weight relative to the total weight of the dispersion as obtained after step 3).

Polyisocyanate Having at Least Three Isocyanate Functional Groups

Suitable polyisocyanates used according to the invention include aromatic polyisocyanate, aliphatic polyisocyanate and mixtures thereof. According to the invention, the oil phase comprises at least one polyisocyanate having at least 3 but may comprise up to 6, or even only 4, isocyanate functional groups.

According to a particular embodiment, a triisocyanate (3 isocyanate functional groups) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

The at least one polyisocyanate used in the process of the invention is present in amounts representing from 1 to 15 wt %, preferably from 1.5 to 12 wt %, more preferably from 2 to 8 wt % and even more preferably from 2 to 6 wt % of the oil phase.

According to a particular embodiment, the oil phase essentially consists of the polyisocyanate with at least 3 isocyanate functional groups, and the hydrophobic active ingredient.

Step 2: Dissolving an Emulsifier in Water to Form a Water Phase

The polymeric shell of the microcapsule according to the present invention is formed by interfacial polymerization in the presence of an emulsifier.

According the invention, the emulsifier is solubilized in water to form a water phase, preferably at pH>5.

According to the invention, the emulsifier can be ionic or non-ionic.

According to the invention, the ionic emulsifier is chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudocollagen, Biopolymer SA-N (INCI name: Hyaluronic Acid (and) Serum Albumen (and) Dextran Sulfate), Pentacare-NA PF (Hydrolyzed Wheat Gluten (and) *Ceratonia Siliqua* (Carob) Gum (and) Aqua (and) Sodium Dextran Sulfate (and) Bis-Hydroxyethyl Tromethamine (and) Phenoxyethanol (and) Ethylhexylglycerin), and mixtures thereof.

According to a preferred embodiment, the ionic emulsifier is chosen in the group consisting of gum Arabic, carboxymethyl cellulose, sodium caseinate, sugar beet pectin and mixtures thereof.

According to the invention, the non-ionic emulsifier is chosen in the group consisting of polyvinyl alcohol, modified polyvinyl alcohol, modified starch, modified cellulose, polysaccharides, and mixtures thereof.

According to a particular embodiment, the non-ionic emulsifier is chosen in the group consisting of polyvinyl alcohol, modified starch and mixtures thereof.

According to any one of the above embodiments of the present invention, the dispersion comprises between about 0.1% and 5% w/w of at least an emulsifier, percentage being expressed on a w/w basis relative to the total weight of the dispersion as obtained after step 3). In still another aspect of the invention, the dispersion comprises between about 0.1% and 2% w/w of at least an emulsifier. In still another aspect of the invention, the dispersion comprises between about 0.1% and 1% w/w of at least an emulsifier.

Step 3: Admixing the Oil Phase and the Water Phase to Form a Dispersion

In the next step of the process of the invention, the oil phase is then added to the water phase to form a dispersion.

According to an embodiment, the mean droplet size is comprised between 1 and 3000 μm leading to microcapsules having a size comprised between 1 and 3000 μm.

The size of the microcapsules can be easily adjusted by the skilled person as a function of the nature of the desired application.

Therefore according to an embodiment, microcapsules have a mean size comprised between 1 and 100 μm, preferably between 5 and 50 microns since they have proved useful for long-lastingness.

According to another embodiment, microcapsules have a mean size greater than 100 microns and 3000 μm, preferably between 300 and 1500 microns since they have proved useful in blooming.

Step 4: Curing Step

This is followed by a curing step 4) which allows to end up with microcapsules in the form of a slurry. According to a preferred embodiment, said step is performed at a temperature comprised between 50 and 130° C., possibly under pressure, for 15 minutes to 8 hours. More preferably it is performed at between 50 and 90° C. for between 30 minutes and 4 hours. Most preferably it is performed between 75 and 90° C. for between 1 and 4 hours.

Optional Steps

Non Cationic Outer Coating

The process of the invention does not comprise a further step of adding a cationic polymer to form an outer coating to the microcapsule.

However, according to a particular embodiment of the invention, at the end of step 4) one may add to the invention's slurry a non-ionic polysaccharide to form an outer coating to the microcapsule.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step 4). It is clearly understood by a person skilled in the art that only part of said added polymers will be incorporated into/deposited on the microcapsule shell.

Drying

According to an embodiment, the slurry obtained by the process described above can be submitted to a drying, like spray-drying, to provide the microcapsules as such, i.e. in a powdery form. It is understood that any standard method known by a person skilled in the art to perform such drying is also applicable.

In particular, the person skilled in the art will be able to select a suitable method for drying notably according to the size of the microcapsules.

As an example, the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

A microcapsule slurry or a microcapsule powder obtainable by a process as defined in any of the above-embodiment is another object of the invention.

Another object of the present invention is a polyurea-based microcapsule slurry comprising microcapsules having a core-shell morphology and comprising an oil-based core comprising a hydrophobic active ingredient;

a shell consisting essentially of polymerised polyisocyanate formed from at least on polyisocyanate comprising at least three isocyanate functional groups in the absence of a polyamine or an amine, and an emulsifier as defined above, wherein the microcapsule does not comprise a cationic coating.

According to the invention, the microcapsules are free from melamine-formaldehyde.

Despite the nature of the polyisocyanate forming the membrane and despite the fact that the membrane is relatively thin in view of the limited amount of polyisocyanate used during the process, the capsules of the invention show very good performance in terms of stability in challenging medium and good olfactive performance.

Another object of the present invention is a perfuming composition comprising:
(i) microcapsules as defined above, wherein the oil comprises a perfume;
(ii) at least one ingredient selected from the group consisting of a perfumery carrier, a perfumery co-ingredient and mixtures thereof;
(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

Another object of the present invention is a liquid consumer product comprising:
a) from 2 to 65% by weight, relative to the total weight of the consumer product, of at least one surfactant;
b) water or a water-miscible hydrophilic organic solvent; and
c) microcapsules as defined above,
d) optionally non-encapsulated perfume.

A powder consumer product comprising
(a) from 2 to 65% by weight, relative to the total weight of the consumer product, of at least one surfactant;
(b) microcapsules as defined above.
(c) optionally perfume powder that is different from the microcapsules defined above is also an object according to the present invention.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powder consumer product comprising:
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

According to a particular embodiment, the consumer product is selected from the group consisting of a shampoo, a shower gel, a rinse-off conditioner, a soap bar, a powder or a liquid detergent, a fabric softener and a floor cleaner.

Preferably, the consumer product comprises from 0.05 wt %, preferably from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

The capsules of the invention have proven to be particularly and advantageously stable in consumer products containing significant amount of surfactant and more particularly they demonstrated an improved stability compared to capsules prepared by using an amine to induce the polymerization of the polyisocyanate.

The invention will now be further described by way of examples. It will be appreciated that the invention as claimed is not intended to be limited in any way by these examples.

EXAMPLES

Note:

Capsules A to H, J, K and L are capsules according to the invention

Capsules I, M and N are outside the scope of the invention for comparison purposes.

Example 1

Preparation of Capsules A to I

Microcapsules A to I were prepared with the following ingredients:

| Ingredient | Capsules A to E Amount [g] | Capsules F Amount [g] | Capsules G Amount [g] | Capsules H Amount [g] | Comparative capsule I Amount [g] |
|---|---|---|---|---|---|
| Oil Phase | 21.7 | 27.0 | 33.7 | 38.6 | 20.9 |
| Perfume oil (perfume A) [1] | variable | 24.3 | 30.4 | 34.8 | 19.65 |
| Polyisocyanate [2] | variable | 2.7 | 3.3 | 3.8 | 1.25 |
| Water phase | 77.72 | 72.6 | 65.85 | 60.98 | 78.61 |
| Guanidine Carbonate [3] | 0 | 0 | 0 | 0 | 0.4 |
| Gum Arabic [4] | 0.98 | 1.12 | 1.21 | 1.35 | 1.16 |
| Water | 76.74 | 71.48 | 64.64 | 59.63 | 77.05 |

[1] see Table 2
[2] Takenate ® D-110N (trimethylol propane adduct of xylylene diisocyanate); origin and trademark from Mitsui Chemicals, 75% polyisocyanate/25% ethyl acetate
[3] origin: Fluka
[4] origin Alland & Robert

TABLE 2

Composition of Perfume A

| Raw mat | % in formula |
|---|---|
| STIRRALLYL ACETATE | 4.5% |
| BENZYL ACETATE | 0.9% |
| ALDEHYDE C10 | 2.1% |
| HEXYLCINNAMIC ALDEHYDE | 14.3% |
| ALLYL CAPROATE | 0.7% |
| Ethyl 2-methyl-pentanoate | 0.9% |
| BENZYL BENZOATE | 35.3% |
| CITRONELLYL NITRILE | 1.8% |
| CORANOL [1] | 5.4% |
| DIHYDROMYRCENOL | 5.4% |
| FRUCTALATE ® [2] | 5.4% |
| HEDIONE ® [3] | 14.9% |
| LIMONENE | 2.4% |
| LINALOOL | 1.0% |
| METHYL METHYLANTHRANILATE | 1.5% |
| PARACYMENE | 1.7% |
| RHUBOFLOR | 0.7% |
| TERPINENE G | 0.6% |
| 2,4-Dimethyl-3-cyclohexene-1-carbaldehyde | 0.6% |
| TOTAL | 100% |

[1] 4-cyclohexyl-2-methyl-2-butanol; origin and Trademark from Firmenich SA, Geneva, Switzerland
[2] 1,4-cyclohexane dicarboxylate de diéthyle; origin and Trademark from Firmenich SA, Geneva, Switzerland
[3] Methyl dihydrojasmonate; origin and Trademark from Firmenich SA, Geneva, Switzerland The variable amounts of the polyisocyanate and perfume used to make the capsule wall of Capsules A to I are summarized in the table 3 below:

TABLE 3

Variable weight of perfume A and Takenate D-110N to prepare capsules A to I

| | A | B | C | D | E | F | G | H | I |
|---|---|---|---|---|---|---|---|---|---|
| Weight of perfume A (g) | 18.87 | 19.55 | 19.55 | 20.1 | 20.4 | 24.3 | 30.3 | 34.8 | 19.65 |
| Weight of Takenate ® D-110N used (g) | 2.83 | 2.15 | 2.15 | 1.6 | 1.3 | 2.7 | 3.3 | 3.8 | 1.25 |
| % of commercial Takenate ® D-110N in oil phase | 15 | 11 | 11 | 8 | 6.4 | 11 | 11 | 11 | 6.4 |
| % of pure polyisocyanate in oil phase | 11.25 | 8.25 | 8.25 | 6 | 4.8 | 8.25 | 8.25 | 8.25 | 4.8 |
| Microcapsule size (microns) | 680 | 600 | 300 | 650 | 615 | 670 | 620 | 640 | 640 |

Process for Making Microcapsules A to I:

The oil phase was prepared by admixing a variable amount of polyisocyanate (trimethylol propane adduct of xylylene diisocyanate, Takenate® D-110N, origin and trademark from Mitsui Chemicals) with a variable amount of perfume oil A in the quantities defined in Tables 1 and 3.

The aqueous phase was prepared by dissolving the gum arabic in water. The emulsion was prepared by dispersing the perfume/polyisocyanate premix oil in the aqueous phase with the stirrer at 230 rpm. pH of the emulsion was measured at 6.7. The temperature was raised to 70° C. and was kept at 70° C. for 1 h30 to allow the curing of the capsules. At this point, capsules were formed, cross-linked and stable. The mixture was left to cool down to room temperature.

For capsules I (outside the invention), a polyamine (guanidine carbonate) was added to the water phase before the temperature was raised to 70° C. so that it could react with the polyisocyanate at the interface to form a polyurea. After encapsulation and use of the Takenate® D-110N to produce the capsule wall, the residual level of unreacted polyisocyanate in the perfume oil was very low and therefore the internal core of the capsule was essentially made of the perfume oil.

The size distribution of the capsules was controlled by Optical Microscopy and Light Scattering (Mastersizer 3000, Malvern).

Example 2

Preparation of Capsules J

The oil phase was prepared by admixing 1.6 g of polyisocyanate (trimethylol propane adduct of xylylene diisocyanate, Takenate® D-110N, origin and trademark from Mitsui Chemicals) with 25.4 g of perfume oil A (compositions defined in Table 2).

The aqueous phase was prepared by dissolving 0.1 g of sugar beet pectin (origin from CP Kelco) in 72.36 g of water. The emulsion was prepared by dispersing the perfume/polyisocyanate premix oil in the aqueous phase with the stirrer at 230 rpm. The temperature was raised to 70° C. and was kept at 70° C. for 1 h30 to allow the curing of the capsules. At this point, capsules were formed, cross-linked and stable. The mixture was left to cool down to room temperature.

After encapsulation and use of the Takenate D-110N to produce the capsule wall, the residual level of unreacted polyisocyanate in the perfume oil was very low and therefore the internal core of the capsule was essentially made of the perfume oil.

The size distribution of the capsules is 640 μm and was controlled by Optical Microscopy and Light Scattering (Mastersizer 3000, Malvern).

Example 3

Preparation of Capsules K

The oil phase was prepared by admixing 2.2 g of polyisocyanate (trimethylol propane adduct of xylylene diisocyanate, Takenate® D-110N, origin and trademark from Mitsui Chemicals) with 19.6 g of perfume oil A (compositions defined in Table 2).

The aqueous phase was prepared by dissolving 1.2 g of modified starch (Hicap-100® origin from Ingredion Inc) in 76.7 g of water. The emulsion was prepared by dispersing the perfume/polyisocyanate premix oil in the aqueous phase with the stirrer at 230 rpm. The temperature was raised to 70° C. and was kept at 70° C. for 1 h30 to allow the curing of the capsules. At this point, capsules were formed, cross-linked and stable. The mixture was left to cool down to room temperature.

After encapsulation and use of the Takenate D-110N to produce the capsule wall, the residual level of unreacted polyisocyanate in the perfume oil was very low and therefore the internal core of the capsule was essentially made of the perfume oil.

The size distribution of the capsules is 540 μm and was controlled by Optical Microscopy and Light Scattering (Mastersizer 3000, Malvern).

Example 4

Stability Performance of Capsules According to the Invention

The stability of capsules according to the invention was studied in a shower gel. The model shower gel base used was composed of 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value. Encapsulated perfume concentration in the shower gel base was equivalent to 0.44%.

The amount of perfume having leaked out of the capsules was measured.

Results are summarized in table 4.

TABLE 4

| | Perfume leakage (%) over storage | | | |
| --- | --- | --- | --- | --- |
| | 1 month | | 2 months | |
| Capsules | RT | 40° C. | RT | 40° C. |
| A | 0 | 1 | 1 | 1 |
| B | 0 | 1 | 0 | 1 |
| C | 1 | 1 | 1 | 1 |
| D | 0 | 0 | 0 | 1 |
| E | 0 | 1 | 0 | 1 |
| F | 0 | 1 | NE | NE |
| G | 0 | 1 | 1 | 1 |
| H | 0 | 0 | NE | NE |
| J | 0 | 0 | 0 | 0 |
| K | 0 | 1 | 1 | 3 |

NE: Not evaluated

It is apparent from these results that the capsules of the present invention are stable in a shower gel base regardless the concentration of polyisocyanate, the concentration of perfume or the size of the capsules.

Comparative Example 5

Stability Performance of Capsules According to the Invention (Capsules E) and Comparison with Capsules I (Not Part of the Invention)

The stability of capsules E (absence of an amine) and comparative capsules I (presence of an amine) was compared in a shower gel. The model shower gel base used was composed of 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Encapsulated perfume concentration in the shower gel base was equivalent to 0.44%.

The amount of perfume having leaked out of the capsules was measured.

Results are summarized in table 5.

TABLE 5

Perfume leakage (%) over storage:

| Capsule | | 1 month | | 2 months | | 3 months | |
|---|---|---|---|---|---|---|---|
| | | RT | 45° C. | RT | 45° C. | RT | 45° C. |
| Comparative I | With amine | 14 | 15 | 31 | 39 | 44 | 45 |
| Capsule E | Without amine | 0 | 1 | 0 | 1 | 0 | 1 |

These stability data underline that the absence of an amine during the process increases significantly the stability performance of the capsules when subjected to highly concentrated surfactant media.

Thus, the present invention provides an optimized process that is not only cost effective but also that is not time consuming.

Example 6

Olfactive Performance of Capsules According to the Invention (Capsules E) and Comparison with Capsules I (Not Part of the Invention)

Capsules were dispersed into a structured shower-gel base having the following composition: 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Encapsulated perfume concentration in shower-gel base is equivalent to 0.20%.

Protocol for Evaluation: by 8 Expert Panelists
1) 1 ml of each shower-gels containing capsules is applied on the forearm:
2) Evaluation of the fragrance intensity on a scale from 1 to 7
3) Lathering step during few seconds. New evaluation of the fragrance intensity on a scale from 1 to 7

Evaluation Scale: (Fragrance Intensity):
1=no fragrance odor; 2=just detectable; 3=weak; 4=moderate; 5=slightly strong; 6=intense; 7=very intense.

Figure 1:
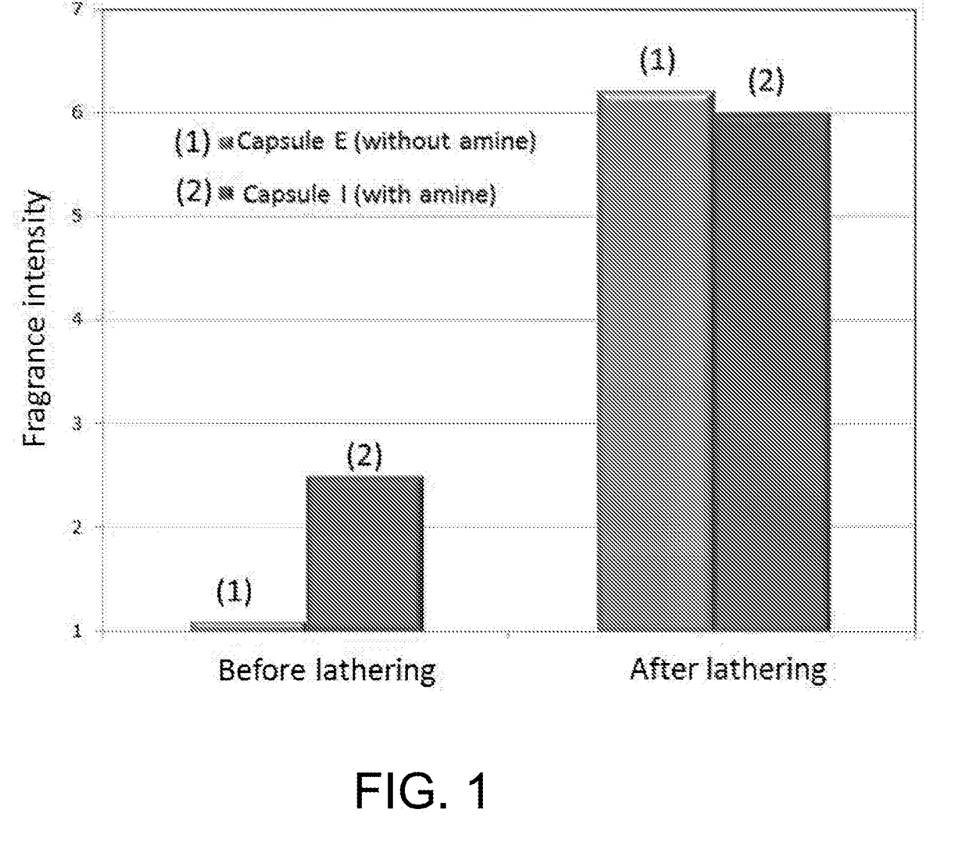
FIG. 1 shows results from an evaluation of capsules in a shower gel composition, with the perfume intensity rated by a panel (capsules prepared without amine [according to the invention] versus capsules prepared with amine [not part of the invention]).

Results
Results are shown on FIG. 1.
One can conclude that:
1) Before lathering, fragrance intensity is higher for capsules I (prepared by using an amine) than for capsules E according to the invention.
2) Similar performance for both capsules I and E after lathering stage.

CONCLUSIONS

These results are consistent with the stability results disclosed in comparative example 5 since it means that a large amount of perfume has leaked out of the capsules I before lathering.

Example 7

Olfactive Performance of Free Oil+Capsules According to the Invention (Capsules B) and Comparison with Only Free Oil Protocol for Evaluation (20 Panelists):
Evaluation in shower/bath cabin of 1) Overall Fragrance Intensity and 2) the Citrus intensity
at the 3 following stages:
1) Neat (from the bottle)
2) In Shower→The panelists wash their body using a normal amount of the product, and turns off the shower during evaluation of the foaming step.
3) After the shower→The panelist steps out of the bathroom or shower cabin for 1 minute then return to evaluate the final intensity.

Fragrance Intensity and Citrus Intensity:
Evaluated on an unlabeled continuous line scale, where 0=Attribute not perceptible odour and 10=very strong intensity for the given attribute.
Data Analysis: Student test analysis ($\alpha=0.05$, paired)
Means with the same letter are not significantly different ($\alpha=0.05$)
Error bars indicate the 95% Confidence Interval.

The model shower gel base used was composed of 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Sample X1 only comprises 0.50% by weight of free oil (perfume A) whereas sample X2 according to the invention comprises 0.50% by weight of free oil and 2% of microcapsules B (0.39% of encapsulated perfume oil).

Figure 2:
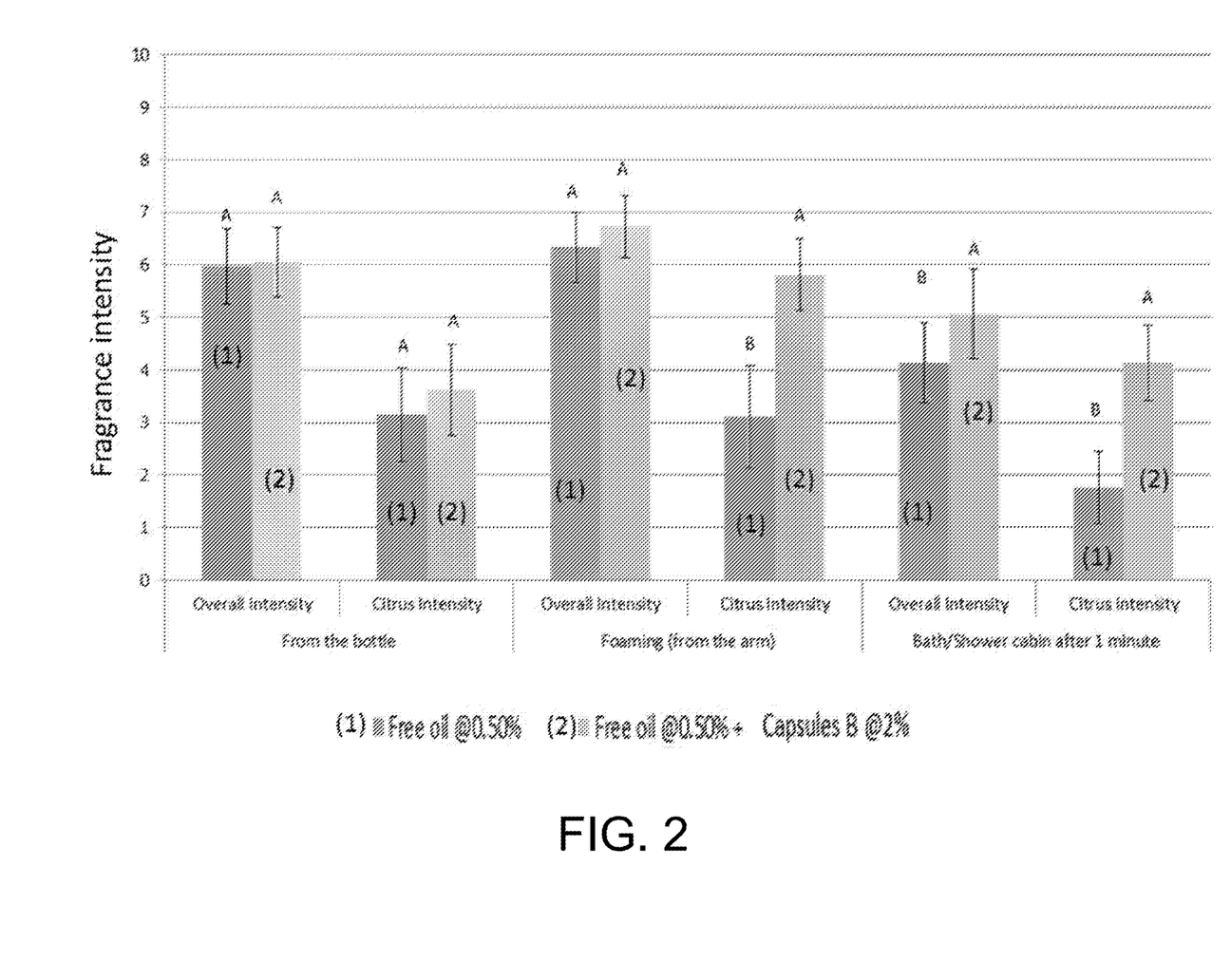
FIG. 2 shows results from an evaluation of capsules in a shower gel composition, with the perfume intensity rated by a panel (free oil with microcapsules according to the invention versus only free oil).

Results are shown in FIG. 2.

These results underline that when smelt neat from the bottle, sample X2 has a similar overall intensity and citrus intensity as sample X1 comprising only free oil.

However:
foaming on the arm, sample X2 is significantly more intense in citrus than the free oil only (sample X1), and
in the bath/shower cabin, sample X2 is perceived to leave both a significantly more citrus and stronger overall fragrance than the free oil only (sample X1).

One can conclude from these results that better olfactive performance are obtained for a composition comprising free oil and capsules according to the invention when compared to a composition comprising only free oil.

Example 8

Olfactive Performance of Capsules According to the Invention (Capsules B and Capsules K) in a Shower Gel Capsules were dispersed into a structured shower-gel base having the following composition: 50% deionized water, 5% thickener (acrylates/beheneth-25 methacrylate copolymer, available from Lubrizol), 43% surfactants (sodium pareth sulfate and cocamidopropyl betaine), 0.5% preservative (sodium benzoate); sodium hydroxide and citric acid are used to adjust the pH value.

Encapsulated perfume concentration in shower-gel base is equivalent to 0.20%.

Protocol for Evaluation: by 8 Expert Panelists
1) Neat (from the bottle)
2) 1 ml of each shower-gels containing capsules is applied on the forearm:
3) Evaluation of the fragrance intensity on a scale from 1 to 7
4) Lathering step during few seconds. New evaluation of the fragrance intensity on a scale from 1 to 7

Evaluation Scale: (Fragrance Intensity):
1=no fragrance odor; 2=just detectable; 3=weak; 4=moderate; 5=slightly strong; 6=intense; 7=very intense.

Figure 3:
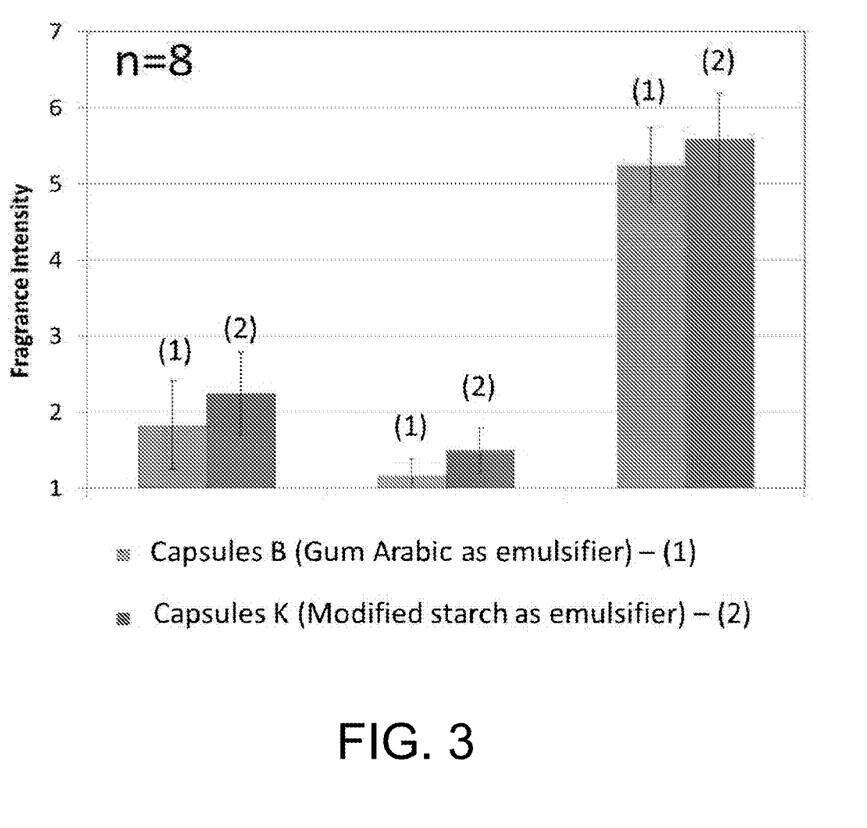
FIG. 3 shows results from an evaluation of capsules (according to the invention) in a shower gel composition, with the perfume intensity rated by a panel.

Results are shown on FIG. 3.

One can conclude that that good olfactive performance is obtained with capsules according to the invention regardless the nature of the emulsifier.

Example 9

Olfactive Performance of Capsules According to the Invention in Kitchen Wipes Test Protocol:

Capsules B were added to standard fragranced kitchen wipe at a dosage of 0.1% (sample A). Wipes used on floor tiles and the intensity of the fragrance released to the air was compared to a reference (Benchmark: standard wipes) and evaluated by 5 panelists after wiping.

Figure 4:
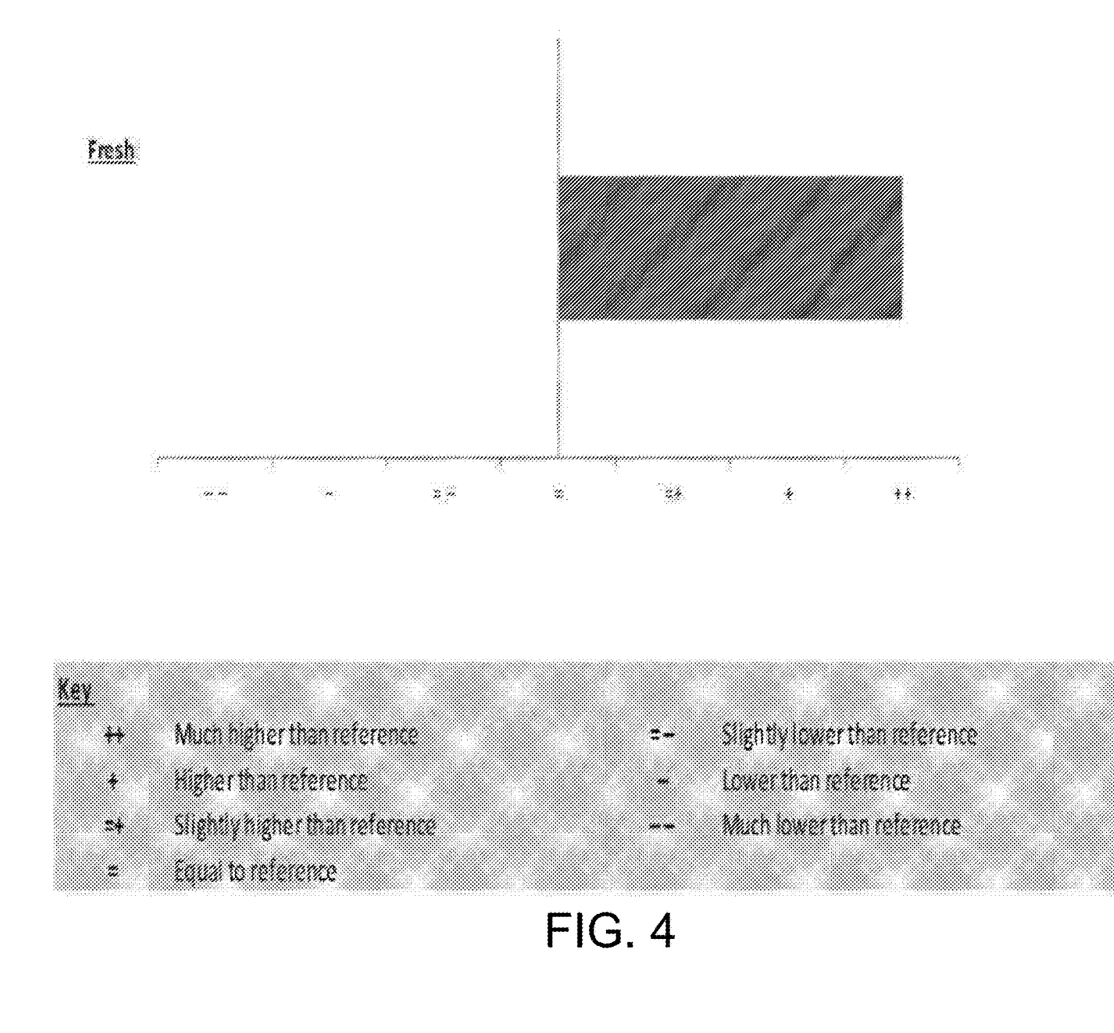
FIG. 4 shows results from an evaluation of capsules in kitchen wipes, with the perfume intensity rated by a panel.

Results:

As shown in FIG. 4, the sample comprising the capsules according to the invention (sample A) delivers much stronger fragrance intensity than standard fragranced wipe (++).

One can note that the intensity is even still strong two hours after wiping.

Example 10

Olfactive Performance of Capsules in AP-Deo

Preparation of Capsules L According to the Invention

The oil phase was prepared by admixing 1.23 g of polyisocyanate (trimethylol propane adduct of xylylene diisocyanate, Takenate® D-110N, origin and trademark from Mitsui Chemicals) with 20.52 g of perfume oil B (compositions defined in Table 6).

The aqueous phase was prepared by dissolving 1.21 g of Gum Arabic (origin from CP Kelco) in 76.67 g of water. The emulsion was prepared by dispersing the perfume/polyisocyanate premix oil in the aqueous phase with the stirrer at 1030 rpm. The temperature was raised to 70° C. and was kept at 70° C. for 1 h30 to allow the curing of the capsules. At this point, capsules were formed, cross-linked and stable. The mixture was left to cool down to room temperature.

After encapsulation and use of the Takenate® D-110N to produce the capsule wall, the residual level of unreacted polyisocyanate in the perfume oil was very low and therefore the internal core of the capsule was essentially made of the perfume oil.

The size distribution of the capsules is 75 microns and was controlled by Optical Microscopy and Light Scattering (Mastersizer 3000, Malvern).

TABLE 6

Composition of perfume oil B

| Raw materials | % |
|---|---|
| 3,7-DIMETHYL-6-OCTENYL ACETATE | 0.8 |
| GERANYL ACETATE (A) + NERYL ACETATE (B) | 0.6 |
| HEXYL ACETATE | 0.8 |
| (1R,2R)-1,7,7-TRIMETHYL-BICYCLO[2.2.1]HEPT-2-YL ACETATE | 0.75 |
| (+−)-1-PHENYLETHYL ACETATE | 0.35 |
| DECANAL | 0.6 |
| DODECANAL | 0.25 |
| 1,4-dioxacycloheptadecane-5,17-dione | 9 |
| (+−)-5-heptyldihydro-2(3H)-furanone | 2.35 |
| BENZYL BENZOATE | 30 |
| (−)-2-methyl-5-(1-propen-2-yl)-2-cyclohexen-1-one | 0.15 |
| (+−)-(3-methoxy-2-methylpropyl)benzene | 0.75 |
| (Z)-3,7-DIMETHYL-2,6-OCTADIENAL (A) + (E)-3,7-DIMETHYL-2,6-OCTADIENAL (B) | 0.1 |
| 4-CYCLOHEXYL-2-METHYL-2-BUTANOL | 3.35 |
| 3-HYDROXY-2-METHYL-4(4H)-PYRANONE | 0.1 |
| tricyclo[5.2.1.0~2,6~]dec-3-en-8-yl acetate (A) + tricyclo[5.2.1.0~2,6~]dec-4-en-8-yl acetate (B) | 2.6 |
| 2-CHROMENONE | 0.35 |
| (+−)-(2E)-1-(2,6,6-trimethyl-2-cyclohexen-1-yl)-2-buten-1-one | 0.05 |
| (+−)-4-DECANOLIDE | 1.45 |
| (2E)-1-[(1RS,2SR)-2,6,6-trimethyl-3-cyclohexen-1-yl]-2-buten-1-one | 0.05 |
| (+−)-2,6-DIMETHYL-7-OCTEN-2-OL | 3 |
| (3Z)-1-[(2E)-2-buten-1-yloxy]-3-hexene (A) + (3Z)-1-[(2Z)-2-buten-1-yloxy]-3-hexene (B) | 0.1 |
| cis-4-(2-methyl-2-propanyl)cyclohexyl acetate (A) + trans-4-(2-methyl-2-propanyl)cyclohexyl acetate (B) | 2.3 |
| 4-(2-methoxy-2-propanyl)-1-methylcyclohexene | 1.3 |
| 1-OXA-12-CYCLOHEXADECEN-2-ONE (A) + 1-OXA-13-CYCLOHEXADECEN-2-ONE (B) | 4.26 |
| benzo[d][1,3]dioxole-5-carbaldehyde | 0 |
| ALLYL HEPTANOATE | 1.25 |
| (+−)-1-(OCTAHYDRO-2,3,8,8-TETRAME-2-NAPHTHALENYL)-1-ETHANONE (DOUBLE BOND: 4A,5 (A) + 4,4A (B) + 4A,8A (C) | 7.55 |
| 1,3-NONANEDIYL DIACETATE (A) + TETRAHYDRO-3-PENT YL-4(2H)-PYRANYL ACETATE (B) | 0.5 |
| (+−)-3,7-dimethyl-1,6-octadien-3-ol | 7.2 |
| 3,6,7-TRIMETHYL-2,6-OCTADIENAL | 0.15 |
| 1-(2-naphthyl)ethanone | 0.1 |
| methyl 2-((1RS,2RS)-3-oxo-2-pentylcyclopentyl)acetate | 3.15 |
| (+−)-ethyl 2-methylbutanoate | 0.25 |
| PERHYDRO-2-CHROMENONE | 0.2 |
| (+)-(2S,4E)-3,3-dimethyl-5-[(1S)-2,2,3-trimethyl-3-cyclopenten-1-yl]-4-penten-2-ol (A) + (+)-(2R,4E)-3,3-dimethyl-5-[(1S)-2,2,3-trimethyl-3-cyclopenten-1-yl]-4-penten-2-ol (B) | 0.1 |
| (2Z)-2-phenyl-2-hexenenitrile | 1.35 |
| (−)-PROPYL (S)-2-(1,1-DIMETHYLPROPOXY)PROPANOATE | 2.95 |
| (+−)-ALPHA-TERPINEOL | 0.8 |
| 3-(4,4-dimethyl-1-cyclohexen-1-yl)propanal | 0.05 |
| (1RS,2RS)-2-(2-methyl-2-propanyl)cyclohexyl acetate (A) + (1RS,2SR)-2-(2-methyl-2-propanyl)cyclohexyl acetate (B) | 7.3 |

TABLE 6-continued

| Composition of perfume oil B | |
| --- | --- |
| Raw materials | % |
| (3E)-4-(2,6,6-trimethyl-1-cyclohexen-1-yl)-3-buten-2-one | 0.55 |
| (1RS,2RS)-2,4-dimethyl-3-cyclohexene-1-carbaldehyde (A) + (1RS,2SR)-2,4-dimethyl-3-cyclohexene-1-carbaldehyde (B) (+−)-2,4-dimethyl-3-cyclohexene-1-carbaldehyde | 0.2 |
| Limonene | 0.22 |
| mixture of methylionones isomers | 0.72 |

Preparation of Comparative Capsules M and N (not Part of the Invention)

Comparative Capsules M

The oil phase was prepared by admixing 2.05 g of polyisocyanate (trimethylol propane adduct of xylylene diisocyanate, Takenate® D-110N, origin and trademark from Mitsui Chemicals) with 40.94 g of perfume oil B (composition defined in Table 6).

The aqueous phase was prepared by dissolving 1.0 g of Gum Arabic (origin from CP Kelco) in 54.8 g of water. The emulsion was prepared by dispersing the perfume/polyisocyanate premix oil in the aqueous phase with the stirrer at 750 rpm.

Then, 0.16 g of guanidine carbonate (origin: Fluka) dissolved in 0.43 g of water were added to the emulsion.

The temperature was raised to 80° C. and was kept at 80° C. for 2 h to allow the curing of the capsules. At this point, capsules were formed, cross-linked and stable. The mixture was left to cool down to room temperature.

After encapsulation and use of the Takenate® D-110N to produce the capsule wall, the residual level of unreacted polyisocyanate in the perfume oil was very low and therefore the internal core of the capsule was essentially made of the perfume oil.

The size distribution of the capsules is 76 microns and was controlled by Optical Microscopy and Light Scattering (Mastersizer 3000, Malvern).

Comparative Capsules N

The oil phase was prepared by admixing 4.92 g of polyisocyanate (trimethylol propane adduct of xylylene diisocyanate, Takenate® D-110N, origin and trademark from Mitsui Chemicals) with 38.6 g of perfume oil B (compositions defined in Table 6).

The aqueous phase was prepared by dissolving 0.53 g of polyvinyl alcohol (Mowiol®18-88, origin from Fluka) in 54.37 g of water. The emulsion was prepared by dispersing the perfume/polyisocyanate premix oil in the aqueous phase with the rotor/stator system. The time and the speed of stirring were adjusted to reach the desired size distribution of the emulsion.

Once the emulsion was prepared, the stirring was continued with the stirrer at 400 rpm till the end of the process.

Then, 0.9 g of guanidine carbonate (origin: Fluka) dissolved in 2.3 g of water were added to the emulsion during 1 hour.

The temperature was raised to 70° C. and was kept at 70° C. for 2 h to allow the curing of the capsules. At this point, capsules were formed, cross-linked and stable. The mixture was left to cool down to room temperature.

After encapsulation and use of the Takenate® D-110N to produce the capsule wall, the residual level of unreacted polyisocyanate in the perfume oil was very low and therefore the internal core of the capsule was essentially made of the perfume oil.

The size distribution of the capsules is 75 microns and was controlled by Optical Microscopy and Light Scattering (Mastersizer 3000, Malvern).

Preparation of AP Roll on Base

A mixture of BRIJ 72 (3.25 g, Croda, UK), BRIJ721 (0.75 g, Croda, UK), and ARLAMOL E (4.00 g, Croda, UK), previously warmed up to 75° C., was added to water (51.00 g) under stirring. The mixture was homogenised for 10 minutes and then cooled down to room temperature under stirring. LOCRON L (40.00 g, Clariant, Switzerland) was added slowly at 45° C., the mixture was kept at room temperature (see table 7). The capsule dispersion of the present invention (circa 2.60 g) was added at 35° C. to afford a white liquid emulsion with the same concentration of encapsulated perfume oil of 0.24% corresponding to 1.17% of capsule slurry for capsules L and 0.59% of capsule slurry for capsules M, a neutral odor (pH 4.2-4.7) and with a viscosity between 1000 and 2500 cPs (measured 24 to 48 h after production).

TABLE 7

| AP Roll on base composition | | |
| --- | --- | --- |
| Raw materials | Amount (g) | % (w/w) |
| BRIJ 72 | 3.25 | 3.17 |
| BRIJ 721 | 0.75 | 0.73 |
| ARLAMOL E | 4.00 | 3.90 |
| Water | 51.00 | 50.70 |
| LOCRON L | 40.00 | 39.00 |
| Capsule dispersion | 2.60 | 2.53 |
| TOTAL | 102.6 | 100 |

A—Stability Performance

Stability performance of capsules L and comparative capsules M was evaluated after 3 months in AP Roll-On base (samples stored at 3° C. and at 45° C.). The evaluation was made by 20 panelists before and after rubbing on a fragrance blotter.

Evaluation Scale: (Fragrance Intensity):

1=no fragrance odor; 2=just detectable; 3=weak; 4=moderate; 5=slightly strong; 6=intense; 7=very intense.

Figure 5:
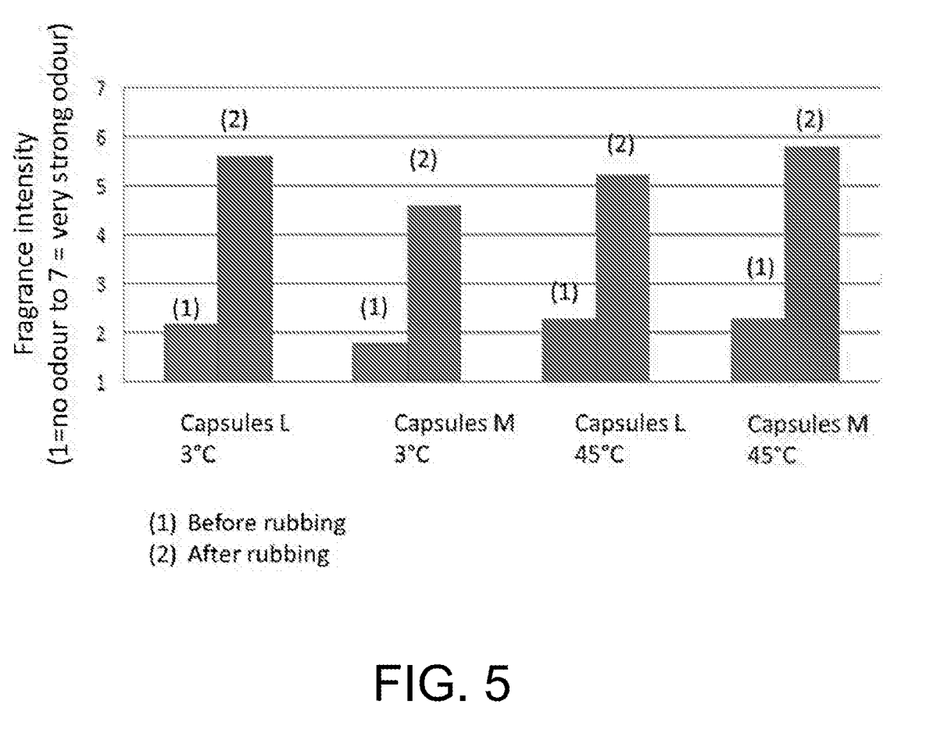
FIGS. 5 and 6 show results from an evaluation of capsules in an Ap-deo roll-on base, with the perfume intensity rated by a panel.

Results are shown on FIG. 5.

One can conclude that the absence of amine in capsules L does not affect the olfactive performance of microcapsules according to the invention in an Ap-deo roll on.

B—Olfactive Performance

The olfactive fragrance intensity in-use application in an AP-deo roll base (see table 7) was evaluated for capsules L and comparative capsules N. The evaluation was made by 24 panelists at different times after application.

Evaluation scale: (Fragrance Intensity):

1=no fragrance odor; 2=just detectable; 3=weak; 4=moderate; 5=slightly strong; 6=intense; 7=very intense.

Figure 6:
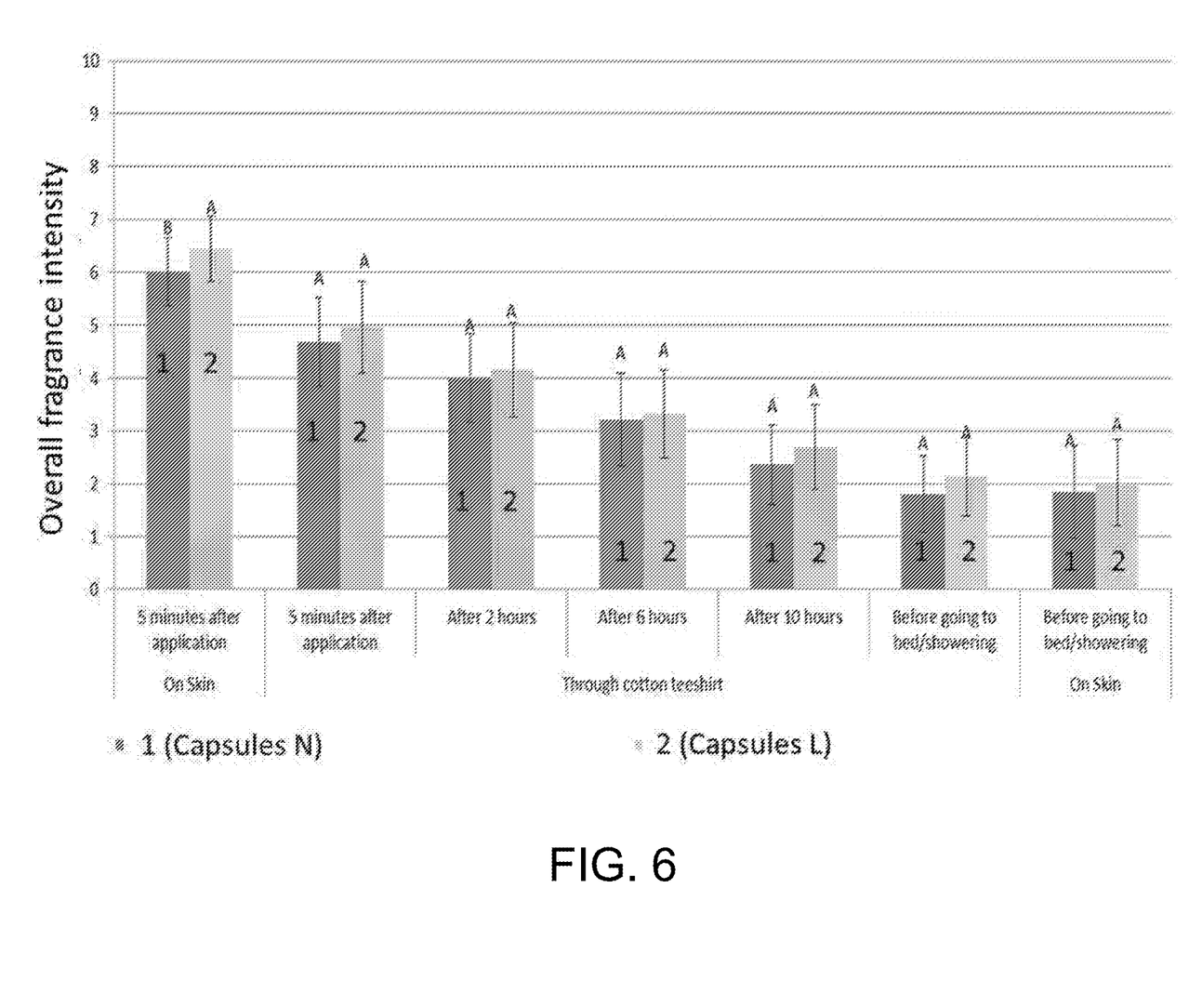

Results are shown on FIG. 6.

One can conclude that the absence of amine in capsules L does not affect the olfactive performance of microcapsules according to the invention in an Ap-deo base.

What is claimed is:

1. A process for the preparation of a polyurea-based core-shell microcapsule slurry comprising the steps of:
  1) admixing a hydrophobic active ingredient with at least one polyisocyanate having at least three isocyanate functional groups to form an oil phase, provided that the oil phase is essentially free from diisocyanate;

2) dissolving an ionic or non-ionic emulsifier in water to form a water phase, wherein the ionic emulsifier is chosen in the group consisting of gum Arabic, carboxymethyl cellulose, soy protein, sodium caseinate, gelatin, bovine serum albumin, sugar beet pectin, hydrolyzed soy protein, hydrolyzed sericin, Pseudo collagen, Biopolymer SA-N, Pentacare-NA PF, and mixtures thereof and wherein the non-ionic emulsifier is chosen in the group consisting of polyvinyl alcohol, modified polyvinyl alcohol, modified starch, modified cellulose, polysaccharides and mixtures thereof;

3) adding the oil phase to the water phase to form an oil-in-water dispersion; and 4) applying conditions sufficient to induce interfacial polymerisation and form microcapsules in form of a slurry;

wherein
the at least one polyisocyanate having at least three isocyanate functional groups is present in an amount comprised between 1 and 15 wt % of the oil phase,
no substantial amount of amine or polyamine is added at any stage of the process,
the process does not comprise a further step of adding a cationic polymer to form an outer coating to the microcapsule, and
no substantial amount of water-soluble reactant is added at any stage of the process, wherein the water-soluble reactant is selected from the group consisting of polyols, thiols, ureas, urethanes and mixtures thereof.

2. The process according to claim 1, further comprising the step of drying the microcapsule slurry to obtain dried microcapsules.

3. The process according to claim 1, wherein the at least one polyisocyanate having at least three isocyanate functional groups is present in an amount comprised between 2 and 8 wt % of the oil phase.

4. The process according to claim 1, wherein the at least one polyisocyanate having at least three isocyanate functional groups is present in an amount comprised between 2 and 6 wt % of the oil phase.

5. The process according to claim 1, wherein the at least one polyisocyanate having at least three isocyanate functional groups is a mixture of at least one aliphatic polyisocyanate and at least one aromatic polyisocyanate, the aliphatic polyisocyanate and the aromatic polyisocyanate being in a respective molar ratio ranging from 80:20 to 10:90.

6. The process according to claim 1, wherein the at least one polyisocyanate having at least three isocyanate functional groups is an aromatic polyisocyanate.

7. The process according to claim 1, wherein the oil phase consists essentially of the hydrophobic active ingredient with the at least one polyisocyanate having at least three isocyanate functional groups.

8. The process according to claim 1, wherein the hydrophobic active ingredient is selected from the group consisting of a perfume, flavor, nutraceuticals, cosmetics, insect control agents, biocide actives and mixtures thereof.

9. A polyurea-based microcapsule slurry obtainable by a process as defined in claim 1.

10. A polyurea-based microcapsule powder obtained by drying the microcapsule slurry as defined in claim 9.

11. The microcapsule slurry according to claim 1 comprising microcapsules having a core-shell morphology and comprising:
an oil-based core comprising a hydrophobic active ingredient wherein the hydrophobic active ingredient is selected from the group consisting of a perfume or flavour oil;
a shell consisting essentially of polymerised polyisocyanate formed from at least one polyisocyanate comprising at least three isocyanate functional groups in the absence of a polyamine or an amine, and an emulsifier as defined in claim 1 and wherein the microcapsules do not comprise a cationic coating.

12. A perfuming composition comprising
(i) a microcapsule slurry as defined in claim 1, wherein the oil comprises a perfume;
(ii) at least one ingredient selected from the group consisting of a perfumery carrier and a perfumery co-ingredient; and
(iii) optionally at least one perfumery adjuvant.

13. A liquid perfumed consumer product, selected from the group consisting of: a laundry care product, a home care product, a body care product, a skin care product, an air care product, and a hygiene product, the consumer product comprising:
a) from 2 to 65% by weight, relative to the total weight of the consumer product, of at least one surfactant;
b) water or a water-miscible hydrophilic organic solvent; and
c) a microcapsule slurry as defined in claim 9.

14. A powder perfumed consumer product, selected from the group consisting of: a laundry care product, a home care product, a body care product, a skin care product, an air care product, and a hygiene product, said consumer product comprising:
a) from 2 to 65% by weight, relative to the total weight of the consumer product, of at least one surfactant; and
b) a microcapsule powder as defined in claim 10.

* * * * *